United States Patent
Weng et al.

(10) Patent No.: US 9,074,974 B2
(45) Date of Patent: Jul. 7, 2015

(54) APPARATUS AND METHOD FOR MEASURING VISCOSITY

(75) Inventors: Huei Chu Weng, Zhongli (TW); Yuan Kai Kao, Yongkang (TW)

(73) Assignee: Chung Yuan Christian University, Chung Li (TW)

( * ) Notice: Subject to any disclaimer, the term of this patent is extended or adjusted under 35 U.S.C. 154(b) by 575 days.

(21) Appl. No.: 13/190,709

(22) Filed: Jul. 26, 2011

(65) Prior Publication Data

US 2012/0022807 A1   Jan. 26, 2012

(30) Foreign Application Priority Data

Jul. 26, 2010 (TW) ................................ 99124601 A

(51) Int. Cl.
  *G01F 17/00* (2006.01)
  *G01N 11/06* (2006.01)
  *G01N 11/04* (2006.01)

(52) U.S. Cl.
  CPC ................ *G01N 11/06* (2013.01); *G01N 11/04* (2013.01)

(58) Field of Classification Search
  CPC ............................. G01N 11/04; G01N 11/08
  USPC .................. 702/50, 45, 55, 138, 140, 48, 47; 73/54.01, 53.01, 54.04, 54.13, 54.11
  See application file for complete search history.

(56) References Cited

U.S. PATENT DOCUMENTS

| | | | | |
|---|---|---|---|---|
| 5,272,912 A | * | 12/1993 | Katsuzaki | ..................... 73/54.08 |
| 8,155,896 B2 | * | 4/2012 | Wargo et al. | .................... 702/50 |
| 2003/0010096 A1 | * | 1/2003 | Long | ............................ 73/54.09 |
| 2011/0126614 A1 | * | 6/2011 | Belitsch | ....................... 73/54.04 |
| 2011/0239744 A1 | * | 10/2011 | Auradou et al. | ............. 73/54.04 |
| 2012/0084024 A1 | * | 4/2012 | Norcross, Jr. | ................... 702/50 |

OTHER PUBLICATIONS

P D Davis, G D Parabrook, G N C Kenny, "Basic Physics and Measurement in anaesthesia", 1995, Butterworth Heinemann, fourth edition, pp. 1-25, 38-40, 141, and 338.*
Henrik Bruus, "Theoretical microfluidics", Fall 2006, DTU, Lecture note third edition, 12-15, 27 and 47.*

* cited by examiner

*Primary Examiner* — Eliseo Ramos Feliciano
*Assistant Examiner* — Eman Alkafawi
(74) *Attorney, Agent, or Firm* — Rosenberg, Klein & Lee

(57) ABSTRACT

An apparatus for measuring viscosity includes a container in which an inlet radius of an inlet end is larger than an outlet radius of an outlet end. A fluid with a flow velocity is placed in the container. The fluid has a density value and a pressure gradient value. A pressure controller for controlling the pressure gradient value of the fluid is connected to the inlet end and the outlet end. A flow meter measures the flow velocity. A viscosity of the fluid is correlated with the density value, the pressure gradient value, the inlet radius, the outlet radius and the flow velocity. After being applied to various fluids, the present invention improves testability. Moreover, the measurement time is reduced due to simple structure. The maintenance is easy and the operation is not complicated. Furthermore, less space is required, the cost is down and the measurement error is reduced.

6 Claims, 3 Drawing Sheets

APPARATUS AND METHOD FOR MEASURING VISCOSITY

BACKGROUND OF THE INVENTION

1. Fields of the Invention

The present invention relates to a measuring apparatus and a measuring method, especially to an apparatus and a method for measuring viscosity.

2. Descriptions of Related Art

Viscosity is one of the important physical properties and is a measure of the resistance of a fluid. The more viscous the fluid is, the lesser its ease of movement. In our daily lives, there are phenomena related to the viscosity such as the taste of drinks, the degree of difficulty in painting, the writing fluency of a fountain pen etc. Among industrial technologies, there are also a lot of applications associated with the viscosity such as a damping device, dip-feed lubrication, fuel oil transfer, and fuel oil atomization etc. The most common viscometers for measuring viscosity available now are followings: rotary viscometers, glass capillary viscometers, and falling ball viscometer.

Take a rotary viscometer as an example. As revealed in U.S. Pat. No. 5,287,732, and No. 6,240,770, a rotary viscometer includes an outer cylinder, an inner coaxial cylinder, and a test liquid in a measuring gap formed between the outer cylinder and the inner cylinder. By rotating the inner cylinder, tangential velocity of the fluid at the wall is changed. Both the torque obtained and the tangential velocity are substituted into Newton's stress-strain equation so as to get the viscosity of the test liquid. The rotary viscometer features on short measurement time, and simple operation. However, the gap between the outer cylinder and the inner cylinder is quite small. Once the fluid such as slurry or suspension contains granules therein, the rotary viscometer doesn't work and its testability is reduced. Moreover, the length of each cylinder is quite long for reducing measurement error. Thus the viscometer occupies space and costs a lot. Furthermore, the length of two cylinders, the gap, location, the shape of the bottom of the cylinder, friction, and residual liquid all have effects on the measurement precision and cause increased measurement error. While measuring viscosity of different fluids, the viscometer needs to be disassembled and cleaned so as to prevent unexpected errors caused by residual fluid. Therefore the management and maintenance of the rotary viscometer are more difficult.

As to the glass capillary viscometer, it includes a U-shaped glass tube with a test liquid therein and two glass bulbs, also known as Ostwald viscometer. One arm of the U-shaped tube is a capillary and the other arm is a normal tube respectively connected to a glass bulb. One glass bulb is lower down than the other one. Due to gravity, the liquid flows in the capillary. The flow rate of the liquid in the capillary is obtained indirectly by control of the level of the liquid in two glass bulbs. By substituting the known flow rate into an equation for viscosity versus flow rate, the viscosity of the test liquid is obtained. Compared with rotary viscometer, the advantage of the glass capillary viscometer is with higher testability, less space and lower cost. However, in order to reduce measurement error, the two glass bulbs should be with larger volume. Moreover, up and down movements of the fluid level take a long time so that the measurement time is extended. Furthermore, the movements of the liquid level in the two glass bulbs cause hydrostatic pressure changes at the outlet end and this influence the measurement precision and further the measurement error is increased. In addition, the capillary diameter is quite small and difficult to be cleaned properly. Thus the maintenance is getting difficult. The liquid level moves freely in the two glass bulbs so that the operation for control of level movement is quite complicated. Besides, once the liquid has high viscosity or granules whose diameter is closed to the capillary diameter, the glass capillary viscometer is not suitable. The testability of the glass capillary viscometer is not high. In order to reduce measurement errors, the volume of each glass bulb is quite large so that the space required is increased. And the capillary is an integrated tube produced with high technical cost. Thus the high cost is still an issue.

Refer to Taiwanese Pat. Pub. No. 200912277, a conventional falling ball viscometer consists of a vertical tube and a ball. A test liquid is in the vertical tube. The ball is allowed to descend through the liquid in the vertical tube due to gravity. A velocity of the falling ball is learned and is substituted into an equation for viscosity versus velocity. Compared with the glass capillary viscometer, its advantages are short measurement time, low instrument cost, and easy operation. However, it's difficult to observe and measure if the test liquid is not clean and transparent. The testability is still not improved. Moreover, the ball size compared with the vertical tube, the surface deterioration and abrasion all have affects on the measurement precision. Thus the measurement error is large. The ball is a consumable and this causes difficulties in maintenance.

In order to overcome above shortcomings, there is a need to provide an apparatus and a method for measuring viscosity that not only improves testability but also reduces measurement time, space required, instrument cost, measurement error, difficulty in maintenance and operation complexity for solving the problems.

SUMMARY OF THE INVENTION

Therefore it is a primary object of the present invention to provide an apparatus and a method for measuring viscosity. By a container in which an inlet end is larger than an outlet end, a formula by which a viscosity value of a fluid is correlated with a pressure gradient value and a flow velocity is derived. The pressure gradient value is modulated by a pressure controller while the flow velocity of the fluid is measured by a flow meter. Thus the viscosity value is obtained according to the pressure gradient value and the flow velocity. The present invention is applied to different fluids with improved testability. Moreover, due to the simple structure, the measurement time is reduced, the maintenance is easy and the operation is not complicated. Furthermore, less space is required, the instrument cost is low, and the measurement error is reduced.

In order to achieve above object, the apparatus for measuring viscosity according to the present invention includes a container, a fluid, a pressure controller and a flow meter. The container has an inlet end and an outlet end. An inlet radius of the inlet end is larger than an outlet radius of the outlet end. The fluid is placed in the container and is flowing with a flow velocity. The fluid has a density value and a pressure gradient value. The pressure controller for control of the pressure gradient value of the fluid is connected to the inlet end and the outlet end. The flow meter measures the flow velocity. A viscosity value of the fluid is correlated with the density value, the pressure gradient value, the inlet radius, the outlet radius and the flow velocity. The present invention has a simple structure so that the maintenance is easy and the operation complexity is low. Moreover, less space is required, the instrument cost is down and the measurement error is reduced.

A method for measuring viscosity of the present invention includes following steps. Firstly, measure an inlet radius of an inlet end of a container and an outlet radius of an outlet end of a container while the inlet radius is larger than the outlet radius. Then modulate a pressure gradient value of a fluid in the container. The fluid in the container is with a certain flow velocity. Next measure the flow velocity. At last, obtain a viscosity value according to a density value of the fluid, the pressure gradient value, the inlet radius, the outlet radius and the flow velocity. The present invention is suitable for various fluids. Not only the testability is increased, the measurement time is also reduced. The convenience in use is further increased.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION OF THE PREFERRED EMBODIMENT

Figure 1:
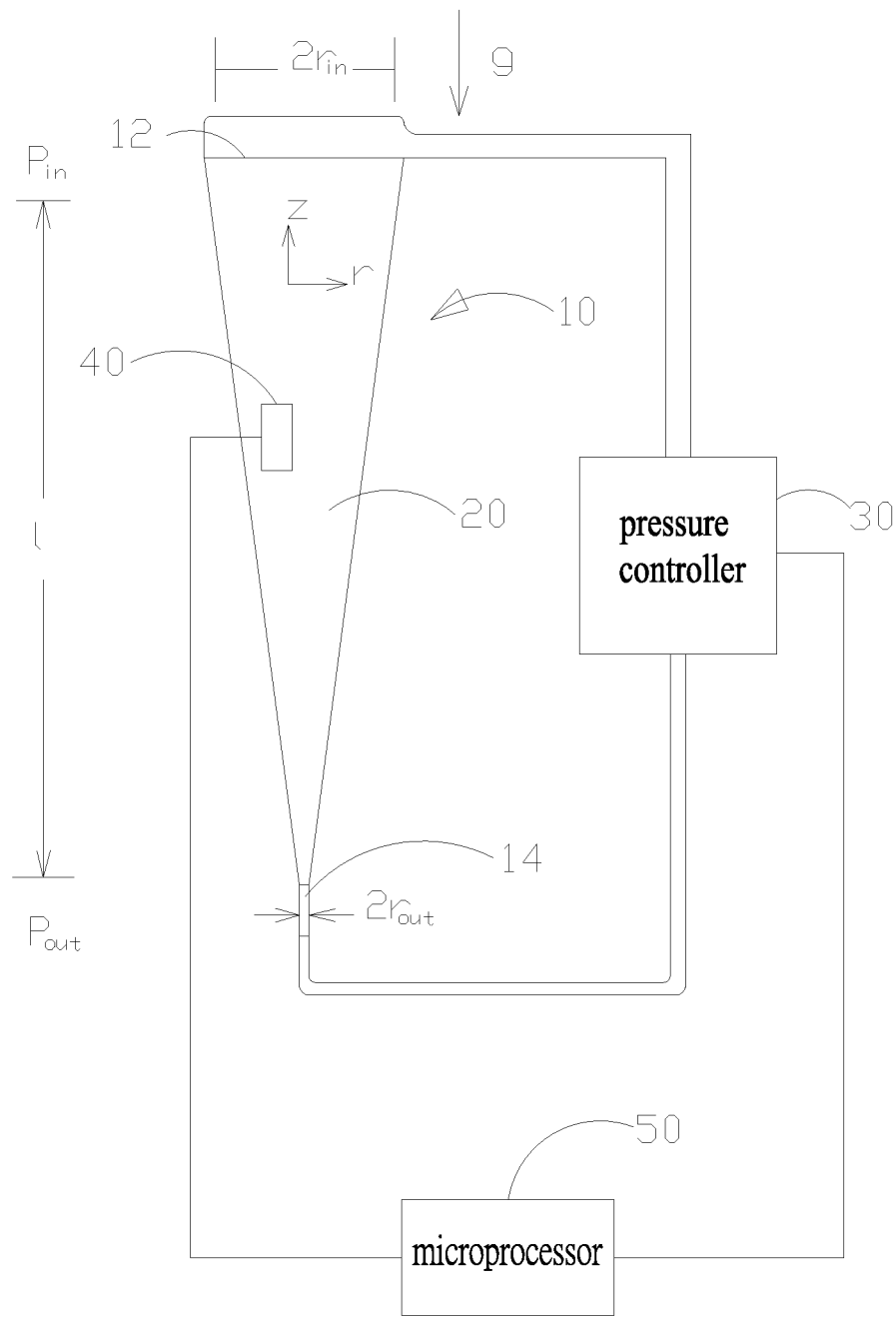
FIG. 1 is a schematic drawing showing structure of an embodiment of an apparatus for measuring viscosity according to the present invention.

Refer to FIG. 1, an apparatus for measuring viscosity of the present invention includes a container 10, a fluid 20, a pressure controller 30 and a flow meter 40. The container 10 is disposed with an inlet end 12 and an outlet end 14 while an inlet radius of the inlet end 12 is larger than an outlet radius of the outlet end 14. The container 10 is with a certain height whose value (height value) is larger than the inlet radius and the outlet radius. The container 10 of the present invention is a reducer in which the fluid 20 is placed. The fluid 20 with a density value of ρ flows out of the outlet end 14 at a flow rate value so that the fluid 20 in the container has a certain flow velocity and a pressure gradient value dp/dz. The pressure controller 30 for control of the pressure gradient value of the fluid 20 is connected with the inlet end 12 and the outlet end 14. The fluid 20 at the inlet end 12 has an inlet pressure $p_{in}$ while the fluid 20 at the outlet end 14 has an outlet pressure $p_{out}$. The difference between the inlet pressure $p_{in}$ and the outlet pressure $p_{out}$ divided by a height l of the container 10 is the pressure gradient value dp/dz.

The pressure controller 30 of the present invention can be a pump, a piston or other devices which can control the pressure so as to control the outlet pressure $p_{out}$ and the inlet pressure $p_{in}$. Thus the pressure gradient value dp/dz is further controlled more precisely. The flow meter 40 is to measure a flow velocity $u_z(r,z)$ of each position in the fluid 20. The viscosity value of the fluid 20 is correlated with the density value, the pressure gradient value, the inlet end radius, the outlet radius and the flow velocity.

Due to gravity and inlet pressure difference between the inlet end and the outlet end, the fluid 20 jets freely from the outlet end 14 while the fluid 20 around the inlet end 12 moves downward slowly. The length of the reducer 10 is larger than the diameter of the inlet and outlet ends 12, 14 so that flow field is represented as the following simplified conservation equation according to mass and momentum balance equations:

$$\frac{1}{r}\frac{\partial}{\partial r}(r u_r) + \frac{\partial u_z}{\partial z} = 0, \\ \frac{dp}{dz} = \mu \frac{1}{r}\frac{\partial}{\partial r}\left(r\frac{\partial u_z}{\partial r}\right) - \rho g. \tag{1}$$

wherein r and z are two coordinates in a cylindrical coordinate system, $u_r$ and $u_z$ respectively are velocity components of r and z, p is pressure, g is acceleration of gravity, ρ is the density value of the fluid 20, μ is viscosity of a test fluid, dp/dz is the pressure gradient value. The momentum conservation equation is integrated twice to obtain the relationship between viscosity and flow rate under the conditions of no sliding ($u_z=0$) and symmetry boundary ($\partial u_z/\partial r = 0$):

$$\mu = \frac{\rho g + dp/dz}{4 u_z(r,z)}\left(r^2 - \left(r_{out} + \frac{r_{in} - r_{out}}{l}(z+l)\right)^2\right) \tag{2}$$

wherein $r_{in}$ and $r_{out}$ respectively is a radius of the inlet end 12 and the outlet end 14 of the container 10, and gravity ρg and pressure gradient dp/dz are sources that drive the fluid 20. In the equation, $(\rho g + dp/dz)/4u_z$ represents a driving force per unit of velocity. In the measurement, geometry of the container 10 and the mathematical statement in the brackets of the equation (2) should be considered. The flow velocity $u_z(r,z)$ obtained of each position of the fluid 20 in the container 10 is substituted into the equation (2) to get the viscosity value of the test fluid 20.

Under the condition that the flow rate through the inlet end 12 and the flow rate through the outlet end 14 are equal, the relationship among the pressure gradient value dp/dz in the equation (2), the inlet pressure $p_{in}$, the outlet pressure $p_{out}$, and a height l of the container 10 is obtained and represented by following equations:

$$\frac{dp}{dz} = 2 b_2 z + b_1 \tag{3}$$

wherein $$b_1 = \frac{(2(p_{in} - p_{out})/l) r_{out}^4 + \rho g (r_{out}^4 - r_{in}^4)}{r_{out}^4 + r_{in}^4}, \quad b_2 = -\frac{p_{in} - p_{out}}{l^2} + \frac{b_1}{l} \tag{4}$$

Moreover, in order to increase the convenience in measuring the viscosity of the fluid 20, the present invention further includes a microprocessor 50 that is electrically connected with the pressure controller 30 and the flow meter 40. The microprocessor 50 substitutes the pressure gradient value dp/dz and the flow velocity $u_z(r,z)$ into the equation (2) for calculation. Thus the structure of the present is simple so that the maintenance is easy and the operation is not complicated. Moreover, less space is required, instrument cost is low, and measurement error is reduced.

Figure 2A:
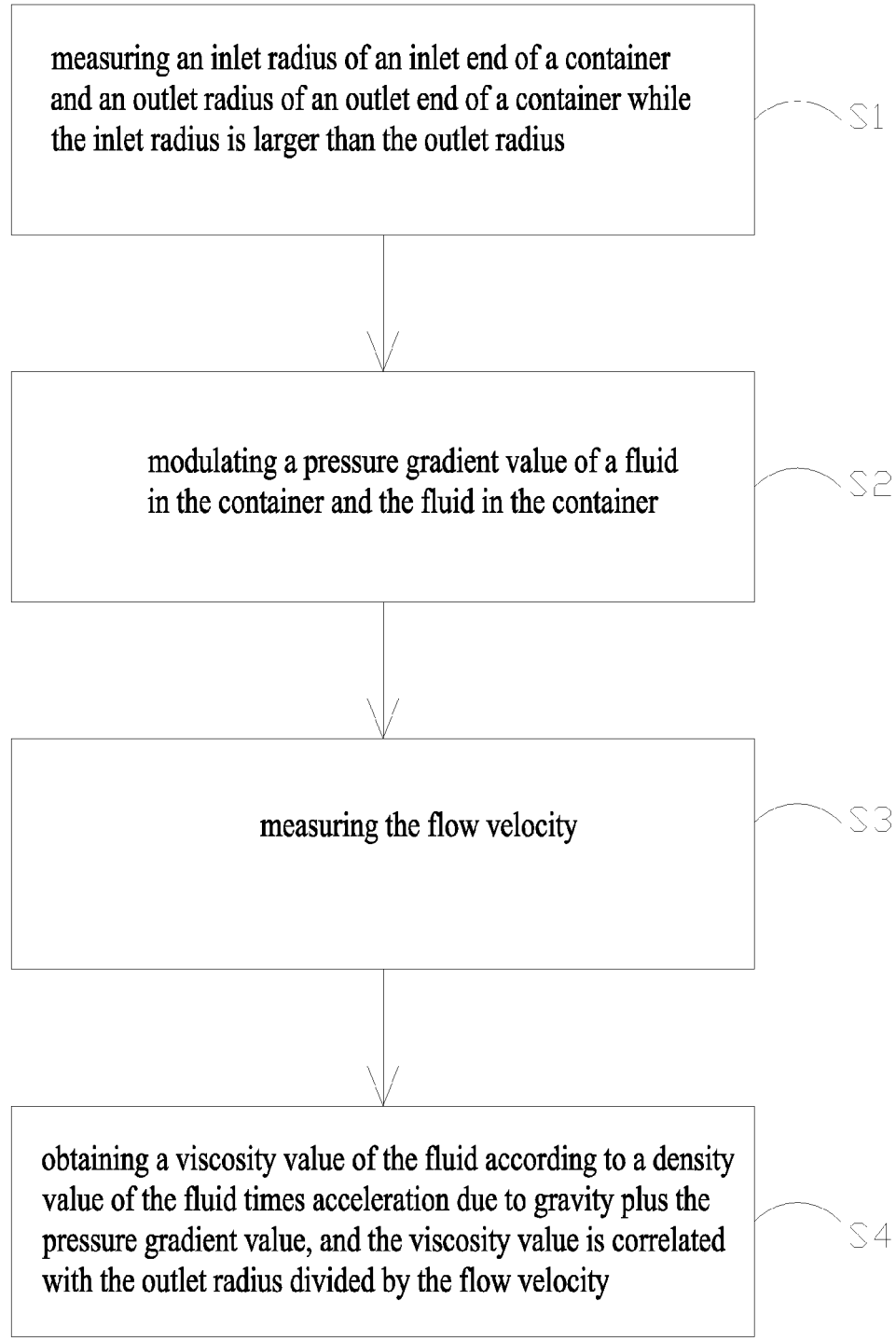
FIG. 2A is a flow chart of an embodiment of a method for measuring viscosity according to the present invention.
Figure 2B:
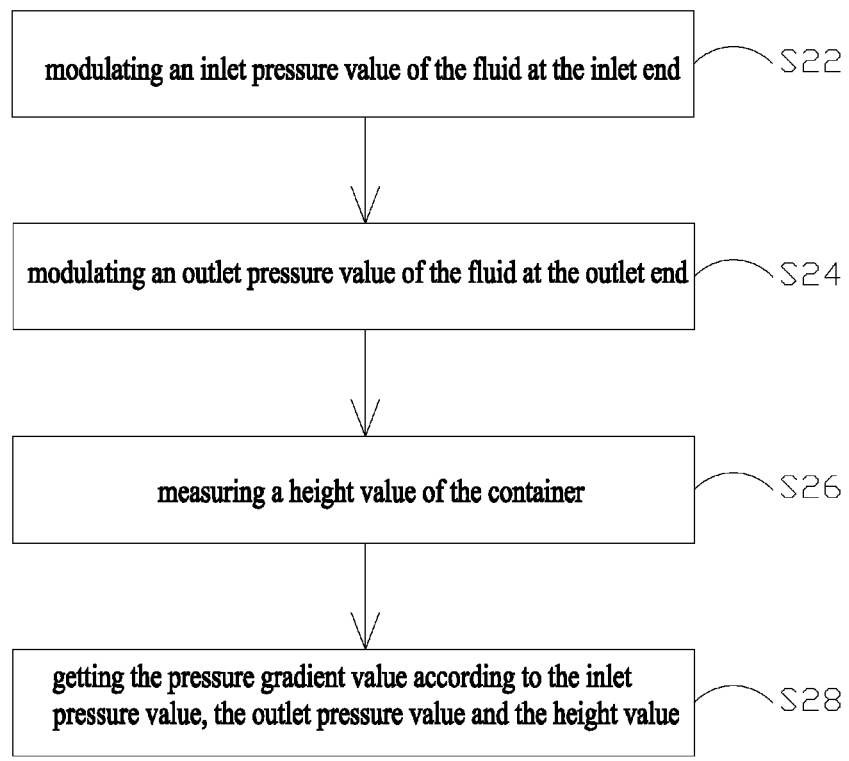
FIG. 2B is a flow chart showing how to measure pressure gradient of an embodiment according to the present invention.

Refer to FIG. 2A and FIG. 2B, a flow chart of a method for measuring viscosity, and a flow chart for measuring pressure gradient are revealed. At first, run the step S1, measure an inlet radius of an inlet end 12 of a container 10 and an outlet radius of an outlet end 14 of a container 10 while the inlet radius is larger than the outlet radius. Then take the step S2, modulate a pressure gradient value of a fluid 20 in the container 10. A pressure controller 30 is used for control of the pressure gradient value. The fluid 20 in the container 10 is with a certain flow velocity. Next take the step S3, measure the flow velocity. Use a flow meter 40 to measure the flow velocity of the fluid 20. Lastly, run the step S4, calculate a viscosity value according to a density value of the fluid 20, the pressure gradient value, the inlet radius, the outlet radius and the flow velocity by means of a microprocessor 50.

The step S2 further consists of following steps. Firstly, take the step S22, modulate an inlet pressure value of the fluid 20 at the inlet end 12. Then run the step S24, modulate an outlet pressure value of the fluid 20 at the outlet end 14. Next refer to the step S26, measure a height value of the container 10. At last, take the step S28, obtain the pressure gradient value according to the inlet pressure value, the outlet pressure value and the height value.

In summary, the present invention provides an apparatus and a method for measuring viscosity. The apparatus for measuring viscosity includes a container, a fluid, a pressure controller and a flow meter. The container is arranged with an inlet end and an outlet end. An inlet radius of the inlet end is larger than an outlet radius of the outlet end. The fluid is placed in the container and is flowing with a flow velocity. The fluid has a density value and a pressure gradient value. The pressure controller for control of the pressure gradient value of the fluid is connected to the inlet end and the outlet end. The flow meter measures the flow velocity. A viscosity value of the fluid is correlated with the density value, the pressure gradient value, the inlet radius, the outlet radius and the flow velocity. The present invention is suitable for different fluids for improving testability. Moreover, the present invention has a simple structure so that the measurement time is reduced, the maintenance is easy and the operation is not complicated. Furthermore, less space is required, the instrument cost is down and the measurement error is reduced.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An apparatus for measuring viscosity comprising: a container disposed with an inlet end and an outlet end while the container is a reducer, and an inlet radius of the inlet end is larger than an outlet radius of the outlet end, and the center of the inlet end and the center of the outlet end are located at the same axis; a fluid placed in the container and having a flow velocity; the fluid has a density value and a pressure gradient value; a pressure controller connected to the inlet end and the outlet end and used for modulating the pressure gradient value of the fluid; and a flow meter that measures the flow velocity; wherein a viscosity value of the fluid is defined by following Expression $$\mu = \frac{\rho g + dp/dz}{4u_z(r,z)}\left(r^2 - \left(r_{out} + \frac{r_{in} - r_{out}}{l}(z+l)\right)^2\right)$$

where, $r_{in}$ and $r_{out}$ respectively is a radius of the inlet end and the outlet end, $\rho$ is fluid density, g is acceleration due to gravity, r, z are two coordinates in a cylindrical coordinate system; I is the height of the container; the $\rho g$ and pressure gradient dp/dz are sources that drive the fluid, and $(\rho g + dp/dz)/4uz$ represents a driving force per unit of velocity.

2. The device as claimed in claim 1, wherein the fluid at the inlet end has an inlet pressure and the fluid at the outlet end has an outlet pressure while a difference between the inlet pressure and the outlet pressure divided by a height value of the container is the pressure gradient value.

3. The device as claimed in claim 1, wherein a height value of the container is larger than the inlet radius and the outlet radius.

4. The device as claimed in claim 1, wherein the apparatus includes a microprocessor that is electrically connected with the pressure controller and the flow meter and is used for calculating the viscosity value.

5. A method for measuring viscosity comprising the steps of: obtaining an inlet radius of an inlet end of a container and an outlet radius of an outlet end of a container while the container is a reducer and the inlet radius is larger than the outlet radius, and the center of the inlet end and the center of the outlet end are located at the same axis; modulating a pressure gradient value of a fluid at the inlet end and the outlet end of the container by a pressure controller, and the fluid in the container having a flow velocity; measuring the flow velocity by a flow meter; and obtaining a viscosity value of the fluid velocity by a microprocessor, the viscosity value of the fluid velocity defined by following Expression;

$$\mu = \frac{\rho g + dp/dz}{4u_z(r,z)}\left(r^2 - \left(r_{out} + \frac{r_{in} - r_{out}}{l}(z+l)\right)^2\right)$$

where, $r_{in}$ and $r_{out}$ respectively is a radius of the inlet end and the outlet end, $\rho$ is fluid density, g is acceleration due to gravity, r, z are two coordinates in a cylindrical coordinate system; I is the height of the container; the $\rho g$ and pressure gradient dp/dz are sources that drive the fluid, and $(\rho g + dp/dz)/4uz$ represents a driving force per unit of velocity.

6. The method as claimed in claim 5, wherein the step of modulating a pressure gradient value of a fluid in the container further includes the steps of:
the pressure controller modulating an inlet pressure value of the fluid at the inlet end; modulating an outlet pressure value of the fluid at the outlet end; measuring a height value of the container; and
getting the pressure gradient value according to the inlet pressure value, the outlet pressure value and the height value by the microprocessor.

* * * * *